(12) United States Patent
Zubkova et al.

(10) Patent No.: US 6,995,201 B2
(45) Date of Patent: Feb. 7, 2006

(54) FLAME RETARDANT FOR POLYMERIC MATERIALS

(75) Inventors: Nina S. Zubkova, Moscow (RU); Nataliya G. Butylkina, Moscow (RU)

(73) Assignee: Isle Firestop Limited, (GB)

( * ) Notice: Subject to any disclaimer, the term of this patent is extended or adjusted under 35 U.S.C. 154(b) by 80 days.

(21) Appl. No.: 10/490,728

(22) PCT Filed: Jul. 16, 2001

(86) PCT No.: PCT/RU01/00293

§ 371 (c)(1),
(2), (4) Date: Mar. 24, 2004

(87) PCT Pub. No.: WO03/008426

PCT Pub. Date: Jan. 30, 2003

(65) Prior Publication Data

US 2004/0259987 A1 Dec. 23, 2004

(51) Int. Cl.
 *C08K 5/5399* (2006.01)
 *C08K 5/5353* (2006.01)
 *C07F 9/44* (2006.01)
(52) U.S. Cl. .................. 524/133; 524/136; 252/609; 558/199
(58) Field of Classification Search ............... 524/133, 524/136; 252/609; 558/199
See application file for complete search history.

(56) References Cited

U.S. PATENT DOCUMENTS

| | | | |
|---|---|---|---|
| 4,732,789 A | 3/1988 | Hauser et al. | |
| 4,750,911 A | 6/1988 | Hansen et al. | |
| 6,863,846 B1 * | 3/2005 | Zubkova et al. | ............ 252/609 |

FOREIGN PATENT DOCUMENTS

| | | |
|---|---|---|
| DE | 36 22 840 | 1/1987 |
| EP | 0 390 109 A2 | 3/1990 |
| EP | 1 116 772 A1 | 8/1999 |
| EP | 1 113 018 | 7/2001 |
| FR | 2 707 308 | 1/1995 |
| RU | 2 024 560 C1 | 6/1991 |
| RU | 2 099 384 C1 | 12/1997 |
| SU | 631336 | 4/1977 |
| SU | 1074886 A | 4/1982 |
| WO | WO 00/14094 | 3/2000 |

OTHER PUBLICATIONS

Brossas; "Fire Retardance in Polymers: An Introductory Lecture"; *Polymer Degradation and Stability* vol. 23; (1989); pps. 313-325.

Camino et al.; "Performance and Mechanisms of Fire Retardants in Polymers—A Review"; *Polymer Degradation and Stability*; vol. 20; (1988) pps. 271-294.

Cusack et al.; "Zinc Hydroxystannate: A Combined Flame Retardant and Smoke Suppressant for Halogenated Polyesters"; *Polymer Degradation and Stability*; vol. 32 (1991): pps. 177-190.

Gnedin et al.; "Phosphorous-Containing Foamed Systems as Retardants of Burning of Polypropylene"; Russian Reference (1991); pps. 621-626 (with English Abstract).

Horrocks; "Developments in flame retardants for heat and fire resistant textiles-the role of char formation and intumescence"; *Polymer Degradation and Stability*; vol. 54 (1996); pps. 143-154.

Levchik et al.; "Mechanistic study of combustion performance and thermal decomposition behaviour of nylon 6 with added halogen-free fire retardants"; *Polymer Degradation and Stability*; vol. 54 (1996); pps. 217-222.

Ma et al.; "Synthesis and Properties of Intumescent, Phosphorus-Containing, Flame-Retardant Polyesters"; Department of Chemistry, Hebei University, Baoding, 071002, China; Received and accepted Jun. 28, 1996; pps. 1511-1515.

* cited by examiner

Primary Examiner—Peter Szekely
(74) *Attorney, Agent, or Firm*—Sheridan Ross PC

(57) ABSTRACT

A flame retardant predominantly of polymeric materials, appearing as a novel chemical compound, viz, ammonium salt of nitrolotris(methylene)phosphonic acid amide.

24 Claims, No Drawings

US 6,995,201 B2

FLAME RETARDANT FOR POLYMERIC MATERIALS

TECHNICAL FIELD

The present invention relates to a process for preparing polymeric materials (woven and unwoven fabrics, carpeting articles, thermoplastic polymers, wood-base materials) featuring reduced flammability, moderate smoke emission, and low-toxicity of the combustion products.

Polymeric materials, including textiles, are used for manufacturing various composite materials, which are then applied in motor vehicles, aircraft industry, and shipbuilding as a decorative and drapery material for furniture upholstering and decorative design of interiors of theatres, museums, and hotels, as well as for domestic uses and for manufacturing overalls.

Widespread use of polymers is restricted due to their high fire hazard.

BACKGROUND ART

Numerous papers devoted to problems of reducing fire hazard of polymeric materials have so far been published. For that purpose flame retardants of various compositions, such as inorganic, halogen- and phosphorus-containing compounds, are used.

Researchers are paying a great deal of attention to the problems of ecological safety of fire-protection materials. A number of firms carry out research work aimed at developing flame retardants and fire-protection technology for polymeric materials that are safe for the environment; in particular, halogen free flame retardant systems are being developed. Toxicological aspect of the problem has been studied extensively, and new FR substances and compositions for polymeric materials have been developed that reduce flammability of the latter and at the same time demonstrate low toxicity and smoke emission.

However, despite the extensive research work performed, the task of reducing flammability of polymers together with minimising smoke emission and combustion product toxicity during pyrolysis of polymers has not yet been solved completely.

Initially, halogenated organic compounds were used for reducing flammability of polymers, mainly aromatic brominated flame retardants, due to their high thermal stability and lower smoke emission compared to aliphatic halogenated compounds. Effectiveness of FR effect of the said flame retardants increases when they are applied together with metal oxides, predominantly with antimony trioxide. In order to reduce smoke emission special additives are used together with the above mentioned systems, most active of which are oxides of aluminium, zinc, and tin [cf. Cusack P. A., 1991, v. 32, #2, pp. 177–190].

However, though smoke emission in the presence of halogen-containing flame retardants may be reduced, the problems of corrosiveness, toxicity, and low resistance to UV-radiation of the compositions obtained are very acute.

The use of halogen containing flame retardants in polymeric materials is restricted due to ecological reasons. Decomposition of polybrominated phenyl ethers gives off dioxines and furanes, which have adverse effect on the ozone layer in the atmosphere thus limiting their application as flame retardants.

Phosphorus containing flame retardants are, to a greater extent, free from the aforementioned disadvantages; in addition, FR effect of phosphorus is three to four times that of bromine (at equal concentrations) (cf. Aseyeva R. A. Combustion of polymeric materials, Moscow, Nauka PH, 1981, p. 249 (in Russian).

To reduce flammability of polymers using phosphorus-containing compounds three principal techniques are applied:

adding flame retardants to a polymer melt;
surface treatment of fabrics and fibres;
chemical modification of polymers.

Adding flame retardants during polymer processing is the most widespread and efficient method of FR protection of polymeric materials, since this method does not require new equipment and is economically effecient. However, application of this method is limited by requirements to a FR additive, i.e. it should be thermally up to 300° C., should dispense easily, have a suitable melting point and high degree of dispersion.

Red phosphorus is a fairly efficient FR for polycaproamide and is used in combinations with metals (cf. Povstugar V. I. Structure and properties of the surface of polymeric materials, Moscow, Khimia PH, 1988, 192 pages (in Russian).

Glass-filled polyamides 6 and 66 modified with a phosphorus-vanadium-containing FR system (with 3–4% phosphorus content in the composition) had the FR class of V—0 with the limiting oxygen index of 28–30%. However, high toxicity and fire hazard of red phosphorus, as well as complexity of the technological process, restricted practical application of the said method.

A number of studies (cf. Levchik G. F. Thermochim. Acta, 1995, v. 257, pp. 117–121) is devoted to reducing flammability of polycaproamide using ammonium polyphosphate (APP) in combination with inorganic additives, in particular, talc, $CaCO_3$, $ZnCO_3$, $MnO_2$.

A disadvantage of this method is in high levels of added to polycaproamide APP—at least 30%, which affects adversely physical and mechanical characteristics of the polymer.

Much attention is given to reducing flammability of polycaproamide by using melamine and its derivatives—cyanuric and isocyanuric acids in combination with metals or phosphorus containing flame retardants (cf. Levchik G. F., Polym. Degrad. Stab., 1996, v. 54, pp. 217–222).

Adding 30% of melamine-isocyanurate to the polymer melt gives a polycaproamide composition with LOI of 27%.

However, as it has been pointed out in a number of papers, adding melamine derivatives to a polycaproamide melt results in higher brittleness of the resultant compositions.

In industry the improved FR performance of polyester (PE) is achieved by adding an oligomer derivative of phenylphosphonic acid (Bisphenol-S, available from Toyobo, Japan, and Eni-Chem, Italy) to the PE melt during molding (cf. Horrocks A. R. Polym. Degrad. Stab., 1966, v. 54, pp. 143–154).

Of great interest for reducing flammability of polyethyleneterephthalate (PETP) is a cyclic phosphonate available from Albright and Wilson under the trade-name of Amgard 1045 (cf. Horrocks A. R. Polym. Degrad. Stab., 1996, v. 54, pp. 143–154). This flame retardant may be used both for finishing textile material and as an additive during processing. Modified fabrics and fibres have LOI of 26–27%.

Most widespread and readily available phosphorus-containing FRs for polyolefins are APP and combinations of APP with polyatomic alcohols and/or melamine (cf. Gnedin Ye. V. High-molecular compounds. Series A, 1991, v. 33, #3, pp. 621–626 (in Russian). These flame retardants are foaming ones, that is, forming highly porous carbonised chars with low heat transfer properties. The use of foaming flame retardant systems increases FR characteristics of polyethylene (PE) and polypropylene (PP). However, for preparing compositions with FR class V—O, FR loading levels should be at least 30%. In addition, in the course of high-temperature processing of compositions containing foaming systems, their components start reacting thus giving off gases that complicate the processing and affect physical and chemical characteristics of the resultant materials.

Micro encapsulated in a polyurethane sheathing APP-FR CROS-484 EC—is available from Bolid GmbH (Germany) (cf. Catalogue of flame retardants. Bolid GmbH, Frankfurt a.M., 1996, 21 pages) is recommended for FR protection of various polymers, including polyolefins.

In the paper by Zubkova N. S. (Plastics, 1996, #5, pp. 35–36) it was proposed to use a micro encapsulated complex of a nitrogen derivative of methylphosphonic acid and ammonium chloride as a flame retardant for polyethylene and polypropylene. However, adding this FR system to polymer melts is difficult because of destruction of microcapsules and evolution of gases, which affect stability of the polymer processing.

A method of surface treatment of polymers which is a further one for reducing their flammability consists in fixing a dissolved, emulsified, or suspended flame retardant additive on a fiber or fabric. The method is comparatively simple and allows of using flame retardants that make part of the composition of finishing agents.

Said composition for fire-protecting finishing may comprise, apart from flame retardants, also promoters, dispersers, dyes, latexes, and so on. To fix flame retardants on a fabric the latter is treated in the presence of methylol compounds or melamine-formaldehyde resins by drying an impregnated fabric at 60–100° C. or heating at 160–170° C. for 2–3 min.

A highly extended class of additives is applicable for imparting fire protecting properties to polymers using said surface-treatment method, comprising phosphorus- and phosphorus-nitrogen-containing compounds, polyphosphates, and some other organic compounds (cf. Sharma V. N., Colourage, 1979, v. 26, #7, pp. 27–33).

Phosphorus-containing flame retardants most frequently used for surface treatment of polycaproamide materials are orthophosphoric acid and esters thereof in combination with epoxy compounds or melamine-formaldehyde resins (cf. FRG Application #3,622,840, IPC C 08 K 5/52).

Most widely used for surface treatment of polycaproamide materials is tetra-(hydroxymethyl)-phosphonium-chloride (THPC) (cf. U.S. Pat. No. 4,750,911). Treatment is carried out jointly with trimethylamine and carbamide under conditions involving heat treatment at 130–140° C., with the resultant undissolvable cross-linked product formed on the fabric surface. A fire-protecting effect is attainable with at least 25% fabric weight increment. However, the burning process of a fabric treated with THPC is accompanied with evolution of toxic phosphine.

Ciba-Geigy AG (Switzerland) produces a composition Pyrovatex-CP recommendable for finishing polyester fabrics and those from a mixture of cellulose and polyester fibres (cf. Shama V. N. Colourage, 1979, v. 26, #7, pp. 27–33). Said composition comprises N-methylol-(O,O-dimethylphosphon-hydroxypropionamide). However, efficiency of fire-protecting effect produced by said composition for fabrics containing above 15% PETP is rather low, because said flame retardant is liable to decompose at a lower temperature compared with that of starting thermooxidative destruction of the original polymer.

The authors of the paper by Camino G. Polym. Degrad. Stab., 1988, v. 20, #3–4, pp. 271–294) propose treating a fabric from PETF and a mixture thereof with cellulose fibres with a composition "Proban" comprising tetra(hydroxymethyl)-phosphonium chloride and polyfunctional nitrogen-containing compounds. However, said composition, similarly to the preceding one, possesses but a low fire-protecting efficiency for fabrics comprising more than 15% of the PETF fibres. To produce fabrics from PETF fibres having reduced flammability, it is recommended that such fabrics be treated with the "Proban" composition at least twice, accompanied additionally with partial phosphorus oxidation into a pentavalent form by treating the dried fabric with an aqueous hydrogen peroxide.

U.S. Pat. No. 4,732,789 discloses a two-stage method of treating PETF fabrics, comprising impregnating the fabric first with the "Proban" composition, then with hexabromocyclododecane or a cyclic phosphonate. Next the thus-treated fabric is subjected to thermofixation; when use is made of hexabromocyclododecane, the fabric is to be heated above 182° C. for the flame retardant to melt down. However, the presence of two stages in the proposed process and a necessity to effect thermofixation of the fabric at high temperatures impede much practical application of the proposed method.

Liquid phosphorus-bromine-containing compositions known under trade name of Antiblaze 315, 345 (cf. Brossas J. Polym. Degrad. Stab., 1989, v. 23, #4, pp. 313–326) are proposed for treating PETF fabrics and finishing textile materials from man-made fibres.

However, the aforementioned compositions may be used for modifying decorative and drapery materials alone, while hardly flammable fabrics may be obtained with a fabric weight increment of at least 30–40% which affects adversely the feel of the fabric and deteriorates physical and chemical characteristics of the materials.

Chemical modification of polymers is performed both at the stage of synthesis thereof and at the stage of finished material and enables flammability of materials to be reduced by changing the structure and properties of macromolecules. Such a modification is most frequently used in the course of polymer synthesis. Said method is in widespread use for treating fireproof PETF fibres (Shovka N. Text Research J., 1993, v. 63, pp. 575–579). There are available from the firm Hoechst in the Federal Republic of Germany fireproof PETF fibres and filaments marketed under various trade marks and produced by copolymerization with phosphorus-containing monomers.

Most widespread are Trevira fibres (FR and CS) used for manufacturing fireproof children's sleeping clothes, upholstery, drapery, and industrial fabrics, as well as curtains an carpets. The fibres are readily dyeable in bright rich hues and are resistant to the effect of direct sunrays.

However, fireproofing characteristics of said fibres are but inadequately high so that with the phosphorus content within 08 and 1.0% the oxygen index equals 26–27%.

With a view to obtaining PETF fibres having reducing flammability, the authors of the paper by Ma Z., J. Appl. Polym. Sci., 1997, v. 63, pp. 1511–1515) propose synthesizing a phosphorus-containing copolymer capable of forming, under the effect of heat flows, a volumetric carbonised layer, i.e., foamed char possessing good heat-insulating properties. Used as a phosphorus-containing copolymer was a phosphorus-containing pentaerythrite derivative. Adding 10% of a phosphorus-containing flame retardant to the PETP polymer chain increases the oxygen index of the composition up to 28%.

A finished polymer can also be modified chemically by treating said polymer with various chemical agents. To attain a high-degree fireproofing, it is necessary to conduct chemical conversions featuring high-degree substitutions, which has an adverse effect on the properties of the resultant materials.

Surface modification of polymeric materials is more economical than the volumetric one, thus presenting a promising way for reducing flammability of many kinds of materials, such as fibres, fabrics, and films.

French Patent #93 08466 discloses the use of a salt of alkylaminomethylenephosphonic acid as a flame retardant for impregnating cellulose fibres and fibres from a mixture of cellulose fibres and polyester fibres; this salt has the following formula:

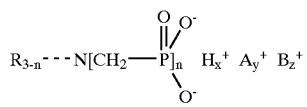

where: R is $CH_3$ or $C_2H_5$;
$H^+$ is hydrogen cation;
$A^+$ are the cations of nitrogen-containing compounds, such as dicyandiamide, guanidine, carbamide and its derivatives;
$B^+$ is ammonium cation;
x is 0 to 6, y is 0 to n, Z is 0 to n;
x+y+Z=2n.

The aforementioned flame retardants were prepared by mixing a respective acid with one of the abovelisted nitrogen-containing compounds in an aqueous medium at a temperature of from 20° C. to the temperature of the salt precipitation. The salts of the abovementioned formula are produced in an aqueous solution with a concentration of from 30 to 60%. For treating cellulose-base fabrics and fabrics from a mixture of cellulose and polyester fibres use was made of aqueous solutions of said salts having a concentration of from 50 to 200 g/l at a pH value of from 2 to 7. After having been impregnated the fabrics were dried. The amount of the flame retardant applied to the fabric depends on its composition and varies from 5% (for cellulose fabrics) to 25% (for fabrics containing up to 50% polyester). A modified fabric did not sustain combustion in the open air. However, a fireproofing effect resultant from the use of said salts is unstable to water treatment procedures.

Selecting one or another method for polymer modification should be determined in each particular case by a required fireproofing efficiency, particularly, it depends on retaining fireproofing characteristics during water treatment procedures (launderings), physical and mechanical properties of the fibres and fibres after treatment, technological particulars and instrumentation of process, as well as technical-and-economical characteristics thereof.

SUMMARY OF THE INVENTION

Despite an extensive research in reduction of flammability of polymeric materials, a great majority of the proposed FR compositions cannot be industrially utilized due to their toxicity, limited availability thereof or to necessity to apply flame retardant in quantities exceeding 25% of the total weight of the fabric or polymer, which results in unacceptable handle of the fabric and poor physico-mechanical properties of the FR treated polymers. That is why the task of providing new efficient flame retardants both for textiles and polymers is a very urgent one. Embodiments of the present invention seek to address these problems.

Other objects of the present invention are as follows:
provision of a non-halogen flame retardant;
reducing toxicity of gaseous products evolving during the combustion process;
possibility of adding a synthesized flame retardant to polymeric composition without modifying technological design for processing original polymers.

The essence of the present invention resides first and foremost in providing a novel chemical compound, that is, an ammonium salt of nitrilotris(methylene)triphosphonic acid amide of formula (1).

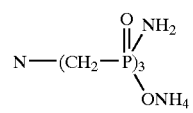

The present compound may be prepared by reacting nitrilotris(methylene)triphosphonic acid with carbamide (urea) in a solid phase at 100 to 200° C. and heating the melt at said temperature for about 12 hours. The resultant compound, according to the present invention, can be used as an efficient flame retardant for predominantly polymeric materials.

Polymeric compositions with reduced flammability, which are based polyethylene, polypropylene, and copolymers of thereof, can be prepared by adding the proposed flame retardant at the stage of polymer processing. In particular, compounded polymer pellets can be produced by simultaneous dispensation of the said flame retardant and the polymer into an extruder with downstream pelletizer.

The proposed flame retardant may be micro encapsulated into a polymeric sheathing, particularly, into polyorganosiloxanes. Micro encapsulating allows to avoid possible evolving of volatile compounds during the compounding stage, and to prevent exudation of the flame retardant later on. The usage of a micro encapsulated flame retardant helps to uniformly distribute the said flame retardant over the bulk of the polymer, which improves the FR properties of the materials without any substantial change in the physical and mechanical properties of the composition.

This invention suggests another practical method for producing FR polymers, such as woven and non-woven fabrics, carpeting and wood-base articles, by surface treatment of said items with the flame retardant.

EXEMPLARY EMBODIMENTS OF THE INVENTION

The following illustrates the present invention by some specific examples of practical application thereof.
Hereinafter:
the Limiting Oxygen Index (LOI) means a minimum oxygen content in the oxygen-nitrogen mixture at which a test sample sustains combustion after the source of ignition has been removed;
class of fire resistance from 0 to 4 was determined in compliance with the State Standard GOST 28157-89;

degree of flammability of fabrics was determined in compliance of the State Standard GOST 50810-95 of the Russian Federation.

Preparing compounds of formula (1).

A total of 299 g of nitrilotris(methylene)triphosphonic acid is thoroughly mixed together with 240 g of urea, which corresponds to a 1:4 molar ratio of the components. The resultant mixture is placed in a temperature-controlled cabinet at 100° C., whereupon the temperature of the reaction therein is gradually increased up to 200° C. and the mixture is heated at this temperature for 12 hours while any by-products of the condensation reaction are continuously removed from the reaction zone. The yield of the synthesized product equals 83% the theoretical value.

Empirical formula: $C_3H_{24}O_6N_7P_3$.

Elementary analysis: found, %: C—10.4; H—7.1; O— . . . ; N—28.0; P—26.9; calculated, %: C—10.4; H—6.9; O—27.7; N—28.2; P—26.8;

EXAMPLE 2

A composition comprising 75 g polypropylene crumb and 25 g the substance prepared according to Example 1 (i.e., flame retardant) is fed into a screw extruder. Extrusion moulding is performed at 220° C. The resultant homogeneous melt is fed to a water bath at 18–25° C., then it is admitted for granulating. Modified polypropylene has LOI of 28.7% and class of fire resistance—0.

EXAMPLE 3

A composition comprising 75 g polycaproamide crumb and 25 g flame retardant prepared according to the present invention is processed as in Example 2. Extrusion moulding is carried out at 230° C. The resultant homogeneous melt is fed to a water bath at 18–25° C., then is admitted for granulating. Modified polycaproamide has LOI of 29.1% and class of fire resistance—0.

EXAMPLE 4

A composition comprising 75 g polyethylene crumb and 25 g flame retardant prepared according to the present invention and micro encapsulated in a polyvinylsiloxane sheathing (its contents making up 4% of the weight of the flame retardant) is processed as in Example 2. The temperature of extrusion molding is 190° C. The resultant homogeneous melt is fed to a water bath at 18–25° C., then is admitted for granulating. Modified polyethylene has LOI of 29.1% and class of fire resistance—0.

EXAMPLE 5

A composition comprising 75 g polycaproamide crumb and 25 g flame retardant prepared according to the present invention and microcapsulated in a polyvinylsiloxane sheathing (its contents making up 4% of the weight of the flame retardant) is processed as in Example 2. The temperature of extrusion moulding is 230° C. The resultant homogeneous melt is fed to a water bath at 18–25° C., then is admitted for granulating. Modified polyethylene has LOI of 29.4% and class of fire resistance—0.

EXAMPLE 6

Fabric from a mixture of cotton yarn and polyester fibres (fibre ratio 35:65) is impregnated with an aqueous solution of flame retardant prepared according to the present invention with a concentration of 200 g/l, dried, and heat-treated at 150° C. Modified fabric has LOI of 32.0% and flammability characteristics as hardly flammable fabric.

EXAMPLE 7

Cotton fabric is impregnated with an aqueous solution of the flame retardant prepared according to the present invention with a concentration of 200 g/l, dried, and heat-treated at 150° C. Modified fabric has LOI of 36.0% and flammability characteristics as hardly flammable fabric.

EXAMPLE 8

Polyester fabric is impregnated with an aqueous solution of the flame retardant prepared according to the present invention with a concentration of 200 g/l, dried, and heat-treated at 150° C. Modified fabric has LOI of 29.5% and flammability characteristics as hardly flammable fabric.

EXAMPLE 9

Polypropylene carpet covering is impregnated with an aqueous solution of the flame retardant prepared according to the present invention with a concentration of 300 g/l and dried at 130° C. The thus-treated carpet covering has LOI of 28.1%.

EXAMPLE 10

Polyamide carpet covering is impregnated with an aqueous solution of the flame retardant prepared according to the present invention with a concentration of 250 g/l and dried at 130° C. The thus-treated carpet covering has LOI of 28.4%.

EXAMPLE 11

Wood test samples measuring 30×60×50 mm according to Standard Specifications NPB 251-98 are impregnated with an aqueous solution of the flame retardant prepared according to the present invention with a concentration of 300 g/l and dried at room temperature. The thus-treated wood test samples are featured by a 6.5% loss in weight, whereby the flame retardants, according to the present invention may be classified among Group I of the fireproofing effectiveness in compliance with Standard Specifications NPB 251-98.

EXAMPLE 12 (COMPARATIVE)

Cotton fabric is impregnated with an aqueous solution of ammonium salt of Nitrilotris(methylene)triphosphonic acid amide with a 100 g/l concentration, dried and heat-treated at 150° C. Modified fabric has LOI of 30.0% and flammability characteristics as hardly flammable fabric.

EXAMPLE 13 (COMPARATIVE)

Polyester fabric is impregnated with an aqueous solution of ammonium salt of Nitrilotris(methylene)triphosphonic acid amide with a 200 g/l concentration, dried and heat-treated 150° C. Modified fabric has LOI of 28.0% and flammability characteristics as hardly flammable fabric.

The invention claimed is:

1. An ammonium salt of nitrilotris(methylene)triphosphonic acid amide of formula (1):

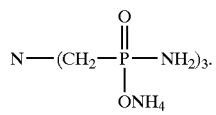

2. A process for preparing an ammonium salt of nitrilotris(methylene)-triphosphonic acid amide of formula 1, comprising reaction of nitrilotris(methylene)triphosphonic acid with urea at a 1:4 molar ratio, under gradual heating of the reaction mixture from about 100 to about 200° C. and keeping the resultant melt at that temperature for about 12 h.

3. A flame retardant comprising polymeric materials, blending with an ammonium salt of nitrilotris(methylene)triphosphonic acid amide of formula (1).

4. The flame retardant of claim 3, wherein it is micro encapsulated in a polymeric sheathing.

5. The flame retardant of claim 4, wherein said polymeric sheathing is made of polyorganosiloxanes.

6. The flame retardant of claim 5, wherein said polyorganosiloxanes are selected from the compounds comprising polyvinylethoxysiloxane or polyvinylacetoxysiloxane.

7. A process for preparing lower-flammability polymeric materials by adding a flame retardant to a polymer in the course of its processing, characterized in that said flame retardant is an ammonium salt of nitrilotris(methylene)triphosphonic acid amide of formula (1).

8. The process of claim 7, wherein the flame retardant is preliminarily microcapsulated into a polymeric sheathing which is based on polyorganosiloxanes.

9. The process of claim 7, wherein the polymer subjected to treatment is polycaproamide.

10. The process of claim 7, wherein the polymer subjected to treatment is polyethylene, polypropylene, or various copolymers based thereon.

11. A method for fireproofing treatment of textile materials comprising the following steps performed in succession:
    impregnating the material with an aqueous solution of ammonium salt of nitrilotris(methylene)triphosphonic acid amide of formula (1),
    drying the material impregnated with the said solution, and
    thermal treatment of the material at a temperature about 140–170° C.

12. The method of claim 11, wherein the materials subjected to the treatment are textile materials from natural fibres.

13. The method of claim 11, wherein the materials subjected to treatment are textile materials from man-made fibres.

14. The method of claim 11, wherein the materials subjected to treatment are textile materials from a mixture of natural and man-made fibres.

15. A method for fireproofing treatment of carpet covering material comprising the following steps performed in succession:
    impregnating the material with an aqueous solution of ammonium salt of nitrilotris(methylene)triphosphonic acid amide of formula (1), and
    drying the material impregnated with said solution, at a temperature of about 120–140° C.

16. The method of claim 15, wherein the carpet coverings subjected to treatment are carpet coverings from mixed man-made fibres.

17. The method of claim 15, wherein the carpet coverings subjected to treatment are carpet coverings from polypropylene or polycaproamide.

18. A method for fireproofing treatment of wood-based articles comprising the following steps performed in succession:
    impregnating the articles with an aqueous solution of ammonium salt of nitrilotris(methylene)triphosphonic acid amide of formula (1), and
    drying the articles impregnated with said solution, at room temperature.

19. A polycaproamide, prepared by the process of claim 9.

20. A polyethylene prepared by the process of claim 10.

21. A polypropylene prepared by the process of claim 10.

22. Textile materials comprising natural and man-made fibres and mixture thereof, treated by the method of claim 11.

23. Carpet coverings comprising man-made fibres, subjected to fireproofing treatment by the method of claim 15.

24. Articles comprising wood treated by the method of claim 18.

* * * * *

UNITED STATES PATENT AND TRADEMARK OFFICE
CERTIFICATE OF CORRECTION

PATENT NO. : 6,995,201 B2  Page 1 of 1
DATED : February 7, 2006
INVENTOR(S) : Zubkova et al.

It is certified that error appears in the above-identified patent and that said Letters Patent is hereby corrected as shown below:

Column 9,
Line 16, delete "blending" and replace with -- blended --.

Signed and Sealed this

Sixth Day of June, 2006

JON W. DUDAS
*Director of the United States Patent and Trademark Office*